US00PP28390P3

(12) United States Plant Patent
Klemm et al.

(10) Patent No.: US PP28,390 P3
(45) Date of Patent: Sep. 12, 2017

(54) ***CALIBRACHOA* PLANT NAMED 'KLECA15327'**

(50) Latin Name: ***Calibrachoa* sp.**
Varietal Denomination: KLECA15327

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 85 days.

(21) Appl. No.: 14/998,726

(22) Filed: Feb. 4, 2016

(65) Prior Publication Data

US 2017/0231143 P1 Aug. 10, 2017

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

PUBLICATIONS

UPOV hit on *Calibrachoa* plant named 'KLECA15327', CA PBR 15-8568, filed Apr. 2, 2015.*

* cited by examiner

*Primary Examiner* — Anne Grunberg
(74) *Attorney, Agent, or Firm* — Barbara Campbell; James M. Weatherly; Cochran Freund & Young, LLC

(57) ABSTRACT

A new *Calibrachoa* plant particularly distinguished by having yellow flowers and a vigorous habit, is disclosed.

1 Drawing Sheet

Genus and species: *Calibrachoa* sp.
Variety denomination: 'KLECA15327'.

BACKGROUND OF THE NEW PLANT

The present invention comprises a new and distinct variety of *Calibrachoa*, botanically known as *Calibrachoa* sp., and hereinafter referred to by the variety name 'KLECA15327'. 'KLECA15327' originated from a controlled cross conducted during summer 2012 in Stuttgart, Germany between the proprietary female *Calibrachoa* variety 'CA-2011-0540' (unpatented) and the proprietary male *Calibrachoa* variety 'CA-2012-0554' (unpatented).

In summer 2012 seed was collected from the controlled cross between the two *Calibrachoa* parental lines. The seeds were sown and plants were grown for evaluation in Stuttgart, Germany. A single plant was selected in May 2013 and was subsequently named 'KLECA15327'. In May 2013, 'KLECA15327' was first vegetatively propagated by tip cuttings. 'KLECA15327' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Yellow flowers; and
2. A vigorous habit.

CROSS-REFERENCE TO RELATED APPLICATIONS

An application for Plant Breeders Rights was filed with the Canadian Plant Breeders Rights Office on Apr. 2, 2015, Application No. 15-8568. 'KLECA15327' has not been made publicly available or sold more than one year prior to the filing date of the instant application.

DESCRIPTION OF THE PHOTOGRAPH

This new *Calibrachoa* plant is illustrated by the accompanying photograph which shows the whole plant, including the habit, the foliage, the flowers, and the buds. The photograph is of a four-month-old plant grown in a pot outdoors in Stuttgart, Germany in August 2014.

The colors shown are as true as can be reasonably obtained by conventional photographic procedures.

DESCRIPTION OF THE NEW VARIETY

The following detailed descriptions set forth the distinctive characteristics of 'KLECA15327'. The data which define these characteristics were collected from asexual reproductions carried out in Stuttgart, Germany. Data was collected on 12-week-old plants grown in a controlled glass greenhouse environment in Stuttgart, Germany in May 2015. Color references are to The R.H.S. Colour Chart of The Royal Horticultural Society of London (R.H.S.) (2007).

Classification:

*Family*.—Solanaceae.
*Botanical*.—*Calibrachoa* sp.
*Common*.—*Calibrachoa*.
*Designation*.—'KLECA15327'.

Parentage:

*Female parent*.—Proprietary *Calibrachoa* line 'CA-2011-0540' (unpatented).

*Male parent*.—Proprietary *Calibrachoa* line 'CA-2012-0554' (unpatented).

Plant:

*Life cycle*.—Annual.
*Form and habit*.—Flat trailing to semi-trailing.
*Height (from soil line to top of foliage)*.—6.0 cm.
*Spread*.—27.0 cm.
*Propagation*.—Vegetatively propagated by tip cuttings.
*Time to produce a rooted cutting*.—3 weeks.

Stems:

*Stem color*.—RHS 144C.
*Pubescence*.—Absent.
*Diameter*.—0.1 cm.
*Length*.—14.0 cm.
*Length, from soil line to first node*.—2.1 cm.
*Total length*.—16.0 cm.
*Internode length*.—1.2 cm.

Leaves:

*Arrangement*.—Alternate, simple, and sessile.
*Shape*.—Elliptic.
*Apex*.—Obtuse to slightly acute.
*Base*.—Attenuate.
*Margin*.—Entire.
*Surface*.—Smooth.
*Surface pubescence*.—Absent.
*Venation*.—Pinnate.
*Venation color*.—Upper surface: RHS 144C. Lower surface: RHS 144D.
*Length*.—2.2 cm.
*Width*.—0.6 cm.
*Color*.—Upper surface: RHS 146A. Lower surface: RHS 147B.
*Fragrance*.—Absent.

Flowers:

*Flower type and habit*.—Single flowers having determinate inflorescence.
*Flowering requirements*.—A minimum of light sun is required.
*Duration of flowers*.—6 days.
*Corolla texture*.—Smooth texture.
*Corolla shape*.—Trumpet-shaped.
*Fragrance*.—Absent.

Flower buds:

*Surface texture*.—Smooth.
*Length*.—2.6 cm.
*Diameter*.—0.9 cm.
*Shape*.—Irregular to oblong.
*Color*.—RHS 4B.

Peduncle:

*Length*.—1.0 cm.
*Diameter*.—0.1 cm.
*Color*.—RHS 144C.
*Texture*.—Smooth.
*Anthocyanin color*.—Absent.

Flower description:

*Flower depth*.—2.6 cm.
*Flower tube length*.—2.3 cm.
*Flower tube diameter*.—0.7 cm.
*Flower diameter*.—4.6 cm.
*Pedicel color*.—RHS 144C.
*Calyx*.—Funnel-shaped.

Sepals:

*Shape*.—Lanceolate.
*Apex*.—Acute.
*Margin*.—Entire.
*Length*.—1.4 cm.
*Diameter*.—0.2 cm.
*Sepal color*.—Upper surface: RHS 143A. Lower surface: RHS 143B.

Petals:

*Shape*.—Heart-shaped.
*Length*.—2.2 cm.
*Apex*.—Obverse.
*Margin*.—Entire, weak undulation.
*Base*.—Open and fused into the tube.
*Pubescence*.—Absent.
*Lobe length*.—2.0 cm.
*Lobe width*.—1.8 cm.
*Lobe color*.—Upper surface: RHS 9B. Lower surface: RHS 3B.
*Corolla tube color*.—Inner: RHS 9A. Outer: RHS 3A.
*Fragrance*.—Absent.

Reproductive organs:

*Stamen number*.—5.
*Stamen color*.—Anther color: RHS 7C. Filament color: RHS N144B. Pollen color: RHS 7C. Pollen amount: Moderate.
*Ovary*.—Placenta arrangement: Ovate. Pistil number: 1. Pistil length: 0.1 cm. Stigma color: RHS 150A. Style length: 0.9 cm. Style color: RHS 150C.

Fruit and seed set: Seed observed sometimes but no additional information on seed is available.

Disease and pest/insect resistance: None observed.

COMPARISON WITH PARENTAL LINES AND KNOWN VARIETY

'KLECA15327' is distinguished from the female and male parental lines as described in Table 1.

TABLE 1

Comparison with Parental Lines

| Trait | 'KLECA15327' | Female parent 'CA-2011-0540' | Male Parent 'CA-2012-0554' |
|---|---|---|---|
| Flower color | RHS 9B | RHS 1A | RHS 55C and RHS 55A |

'KLECA15327' is most similar to the commercial *Calibrachoa* plant named MINIFAMOUS 'Neo Yellow' (unpatented). Differences between the two varieties are described in Table 2.

TABLE 2

Comparison with Similar Variety

| Trait | 'KLECA15327' | MINIFAMOUS 'Neo Yellow' |
|---|---|---|
| Flower color | RHS 9B | RHS 7C |

We claim:

1. A new and distinct variety of *Calibrachoa* plant named 'KLECA15327' as illustrated and described herein.

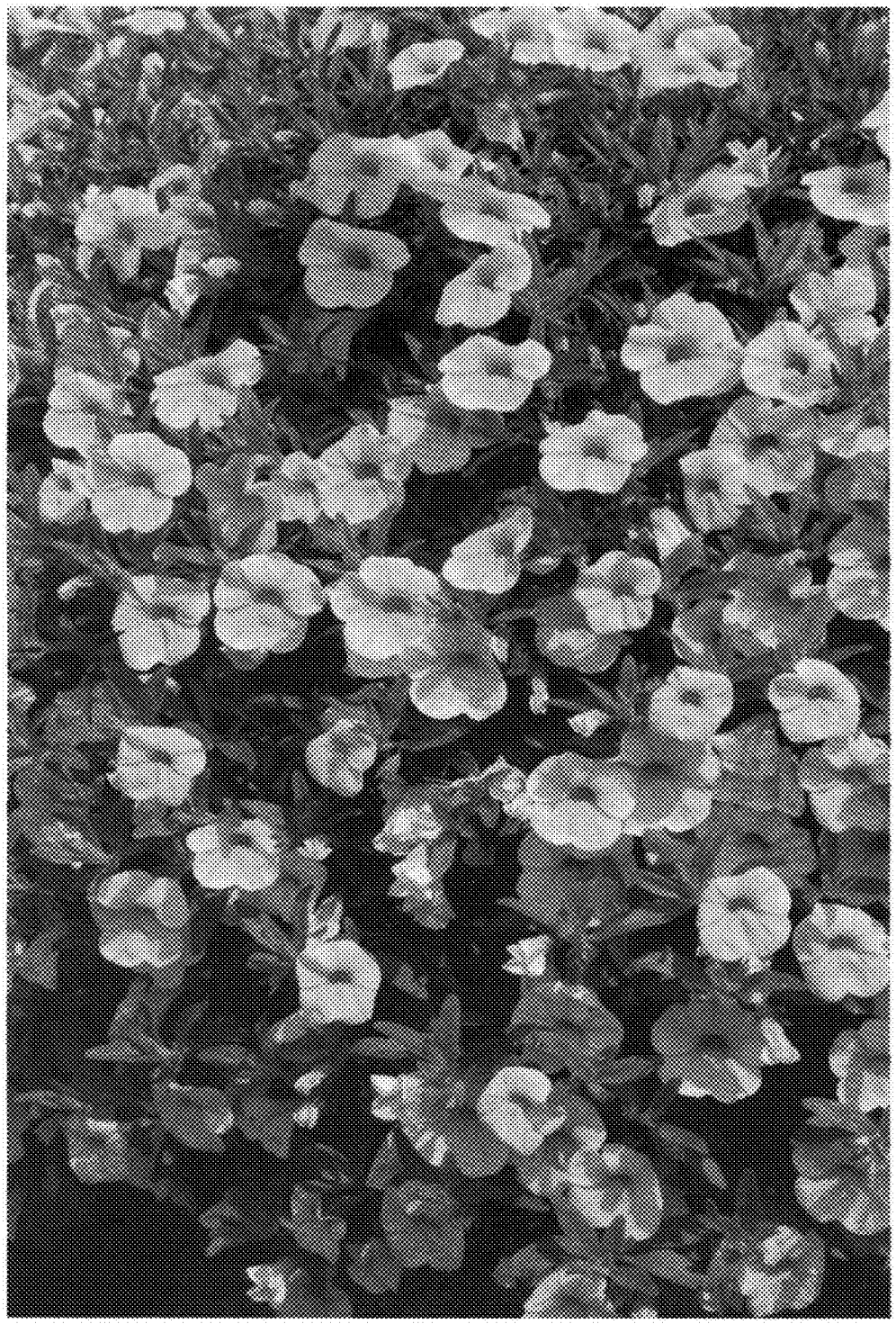

* * * * *